(12) United States Patent
Liang (10) Patent No.: US 8,163,797 B2
(45) Date of Patent: Apr. 24, 2012

(54) METHOD OF TREATING WITH STABLE PRAVASTATIN FORMULATION

(75) Inventor: Alfred Liang, Edison, NJ (US)

(73) Assignee: Actavis Elizabeth LLC, Elizabeth, NJ (US)

( * ) Notice: Subject to any disclaimer, the term of this patent is extended or adjusted under 35 U.S.C. 154(b) by 763 days.

(21) Appl. No.: 10/841,389

(22) Filed: May 7, 2004

(65) Prior Publication Data

US 2005/0143460 A1     Jun. 30, 2005

Related U.S. Application Data

(60) Provisional application No. 60/533,707, filed on Dec. 31, 2003.

(51) Int. Cl.
*A01N 37/00* (2006.01)
*A61K 31/21* (2006.01)

(52) U.S. Cl. ......... 514/513; 514/506; 514/548; 560/256

(58) Field of Classification Search ............... 514/183
See application file for complete search history.

(56) References Cited

U.S. PATENT DOCUMENTS

| | | | |
|---|---|---|---|
| 4,346,227 A | 8/1982 | Terahara et al. | |
| 4,406,888 A * | 9/1983 | Aguiar et al. | 514/298 |
| 5,030,447 A | 7/1991 | Joshi et al. | |
| 5,180,589 A | 1/1993 | Joshi et al. | |
| 5,356,896 A | 10/1994 | Kabadi et al. | |
| 5,830,695 A * | 11/1998 | Serizawa et al. | 435/69.1 |
| 6,503,918 B2 * | 1/2003 | Yoshinari et al. | 514/277 |
| 6,531,507 B1 | 3/2003 | Pflaum et al. | |
| 6,558,659 B2 | 5/2003 | Fox et al. | |
| 6,680,341 B1 * | 1/2004 | Kerc | 514/547 |
| 7,642,286 B2 * | 1/2010 | Li et al. | 514/547 |
| 2002/0035142 A1 * | 3/2002 | Fox et al. | 514/423 |
| 2002/0055533 A1 * | 5/2002 | Kohama et al. | 514/423 |
| 2003/0158097 A1 * | 8/2003 | Tanida et al. | 514/11 |
| 2004/0115265 A1 * | 6/2004 | Benkerrour et al. | 424/471 |

FOREIGN PATENT DOCUMENTS

WO    WO 03/063836    *    7/2003

OTHER PUBLICATIONS

Walters et al., What Do the Statin Trials Tell Us?, 2001, The American Journal of Managed Care, vol. 7, No. 5, Sup, S138-143.*

* cited by examiner

*Primary Examiner* — Jeffrey S. Lundgren
*Assistant Examiner* — Meghan Finn
(74) *Attorney, Agent, or Firm* — Carol Larcher; Larcher & Chao Law Group (57) ABSTRACT

The present invention provides oral pravastatin formulations comprising a physical mixture of pravastatin and at least one pharmaceutically-acceptable excipient, wherein the composition for at least 6 months after its preparation is stable and has a pH of greater than about 7 to less than 9, as well as methods for the preparation and use of these stable formulations.

8 Claims, 4 Drawing Sheets

Figure 1. Typical Sample Chromatogram by HPLC

Figure 2. Typical Spectrum Index for Impurity A by Diode Array

Figure 3. Typical Spectrum Index for Pravastatin by Diode Array

Figure 4. Typical Spectrum Index for Lactone by Diode Array

METHOD OF TREATING WITH STABLE PRAVASTATIN FORMULATION

CROSS-REFERENCE TO RELATED PATENT APPLICATIONS

This patent application claims priority to and the benefit of U.S. Provisional Application No. 60/533,707, filed Dec. 31, 2003, which is incorporated by reference.

FIELD OF THE INVENTION

This invention relates to stabilized pravastatin pharmaceutical compositions, a process for their preparation, and therapeutic methods of use.

BACKGROUND OF THE INVENTION

Pravastatin, having the chemical designation [1S-[1α(βS*, δS*),2α,6α,8β-(R*),8aα]]-1,2,6,7,8,8a-Hexahydro-β,δ,6-trihydroxy-2-methyl-8-(2-methyl-1-oxobutoxy)-1-naphthaleneheptanoic acid, was originally disclosed by Terahara et al. in U.S. Pat. No. 4,346,227. This compound, typically included as a sodium salt in pharmaceutical formulations, is known to function as a lipid-lowering compound. In a commonly accepted mechanism of action, pravastatin inhibits cholesterol biosynthesis by inhibiting HMG-CoA reductase, an enzyme that catalyzes an early rate-limiting step in cholesterol biosynthesis, i.e., the conversion of HMG-CoA to mevalonate. This inhibition, and resulting reduction, in cholesterol levels in humans is desirable, particularly in those individuals having hyperlipidemia, or those having experienced, or who are believed to be susceptible to experiencing, coronary or cardiovascular events.

Pravastatin sodium is marketed in the form of tablets for oral administration in 10 mg, 20 mg, 40 mg and 80 mg strengths. These tablets are currently indicated in the prevention of coronary events, (b) the secondary prevention of cardiovascular events; and (c) hyperlipidemia.

One property affecting the formulation of pravastatin is its tendency to become unstable and degrade, forming lactone as a degradation product, upon exposure to certain environmental conditions (e.g., acidic environments) or pharmaceutical excipients. Despite precautions, pravastatin degradation is so prevalent that the shelf life of current pravastatin formulations is limited at present to 3 years from the date of manufacture.

Prior efforts to limit pravastatin degradation in pharmaceutical formulations involved providing a formulation with a highly alkaline pH, i.e., greater than 9. This was accomplished by including basic components (e.g., buffering agents) in the formulations in amounts effective to provide the formulation with the desired alkaline pH. Illustrative of these basic components include magnesium oxide, aluminum oxide, an alkali metal hydroxide such as sodium hydroxide, potassium hydroxide or lithium hydroxide, or an alkaline earth metal hydroxide such as calcium hydroxide or magnesium hydroxide. Commonly, these components constitute up to about 75 wt. % of the oral dosage form.

However, formulations having this relatively high pH are potentially harmful to the gastric mucosa of patients. Further, the inclusion of certain binders, fillers, disintegrants, lubricants, coloring agents, and other commonly used excipients was found to cause the pravastatin to become unstable and degrade, even when the formulation was prepared to exhibit a highly alkaline pH (i.e., a pH in excess of 9).

Other efforts to limit pravastatin degradation in oral pharmaceutical formulations required processing of the pravastatin prior to preparing the finished formulation. These processes included co-crystallization and/or co-precipitation of the pravastatin with a basifying agent to form a finely distributed homogenous component. Processes of this type, however, are costly, and also require the use of organic solvents that may pose hazards to workers during processing, and which must be removed from the finished formulation.

Thus, despite prior efforts, there remains a need for oral pravastatin formulations, and processes for their preparation and use, that have a relatively neutral pH, in which the pravastatin remains substantially stable, and that do not require processing that is relatively costly, unduly complicated, or use potentially hazardous organic solvents in the preparation of the formulations.

The present invention meets the aforesaid and other needs, as will be apparent from the description of the invention provided herein.

BRIEF SUMMARY OF THE INVENTION

The present invention provides, in one embodiment, an oral pravastatin composition comprising a physical mixture of pravastatin and at least one pharmaceutically-acceptable excipient, wherein the composition for at least 6 months after its preparation is stable and has a pH of greater than about 7 to less than 9.

In a related embodiment, the invention provides a stable oral pravastatin composition comprising a physical mixture of pravastatin and at least one pharmaceutical excipient, wherein the composition for at least 6 months after its preparation, after being placed in a sealed container, comprises less than about 2% lactone after residing for 3 months in a stability chamber set at 40° C. and 75% relative humidity.

A further embodiment of the invention provides an oral pravastatin composition comprising pravastatin, wherein the composition for at least 6 months after its preparation, after being placed in an unsealed container, comprises less than about 0.34 wt. % of a heretofore unknown impurity (referred to herein as Impurity A) after residing for 1 week in a stability chamber set at 55° C. and 75% relative humidity.

Related embodiments of the invention include processes for preparing the aforesaid stable oral pravastatin compositions, wherein these processes comprise physically mixing pravastatin and at least one pharmaceutically-acceptable excipient in amounts sufficient to provide the composition with a pH of about 7 to less than 9, and forming the mixture into an oral composition.

Methods for using the aforesaid stable oral dosage forms of pravastatin are also contemplated in other embodiments of the invention, the methods comprising administering a therapeutically effective amount of pravastatin as provided in the inventive stable oral dosage compositions to a human in the prevention of coronary events, in the secondary prevention of cardiovascular events, or in hyperlipidemia therapy.

DETAILED DESCRIPTION OF THE INVENTION

The present invention provides stable oral dosage formulations of pravastatin, processes for their preparation and methods for their use, that overcome disadvantages present in known formulations, processes and methods of use.

Exemplary of the benefits provided by the present invention relative to existing formulations are a decrease in the pH of the formulation without an unacceptable loss in stability of pravastatin and/or formation of Impurity A above acceptable levels, and ease of processing accompanied by a reduction in cost.

The present invention provides the foregoing and other benefits by, in one embodiment, providing an oral pravastatin composition comprising a physical mixture of pravastatin and at least one pharmaceutically-acceptable excipient, wherein the composition for at least 6 months (and desirably for at least 12 months, more desirably for at least 18 months, preferably for at least 24 months, more preferably for at least 30 months, and most preferably for at least 36 months) after its preparation is stable and has a pH of greater than about 7 to less than 9.

Each embodiment of the present invention includes pravastatin. A reference to pravastatin herein, unless otherwise indicated, includes pravastatin per se and, desirably, pharmaceutically-acceptable salts of pravastatin, such as pravastatin sodium (a preferred salt). Salts were found to provide more favorable physiochemical properties, e.g., solubility, and thus are preferred forms of pravastatin relative to pravastatin per se.

In addition to describing the chemical nature of the active ingredient used in the present invention, the term pravastatin as used herein should be understood as also incorporating certain physical attributes of this active. Specifically, the term pravastatin used herein also describes an active that has not been subjected to preformulation processing that combines pravastatin with an excipient, typically a solid excipient, e.g., coprecipitation or co-crystallization. One of the perceived advantages of the present invention is the ability to prepare stable oral pharmaceutical formulations of pravastatin by combining the various components of the formulation and unprocessed pravastatin via physical mixing, e.g., granulation (e.g., wet granulation, dry granulation, fluid-bed granulation), spheronization, spray-drying, spray-congealing, with the resulting mixed composition being subsequently formed into the desired oral dosage form. Direct compression of the mixed components is also contemplated in the present invention, and may be used. It is believed that, in excluding the preformulation processing of pravastatin, and in using physical mixing of the various formulation components, the inventive formulations and processes provide time and cost advantages relative to existing formulations and processes.

The pravastatin included in the present invention is, desirably, included in an amount sufficient to prevent or treat an illness or condition afflicting an animal, particularly humans. Thus, while the amount of pravastatin in the inventive formulations is not necessarily limited, one should be cognizant of including amounts of pravastatin and excipients that together will result in an oral formulation having the desired pH. Generally, the amount of pravastatin that may be included therein may range from about 1 to about 60 wt. % of the formulation, desirably from about 5 wt. % to about 50 wt. %, more desirably from about 10 wt. % to about 20 wt. %, to about 30 wt. % or to about 40 wt. %. In absolute terms, the amount of pravastatin in a single oral formulation may range from about 1 mg to about 120 mg, and may desirably range from about 10 mg to about 80 mg. Preferably, the pravastatin in single oral dosage formulations is provided, most preferably as a sodium salt, in amounts of about 10 mg, 20 mg, 40 mg or 80 mg.

One aspect of the invention is that the inventive oral formulations have one or more properties (e.g., pH, stability) for a certain period of time after preparation of the composition. The preparation date of the composition is when the pravastatin-containing composition is converted into a finished form for administration, e.g., when tablets are formed by a tableting device. If this cannot be determined, one may obtain the preparation date by subtracting the period during which the oral formulation is approved for sale from the expiration date of the formulation.

In each embodiment of the present invention, the stable oral pharmaceutical formulations contemplated therein have a pH that is lower relative to that exhibited by existing pravastatin oral formulations. In this regard, the pH of the inventive formulations may range from about 7 to less than 9. Desirably, however, the pH range of the formulation is closer to 7 than 9. The pH thus ranges more desirably from about 7 to about 8.5, more desirably from about 7 to about 8, and still more desirably from about 7 to about 7.5. Preferably, the pH ranges from about 7 to about 8.7, more preferably from about 7.0 to about 8.3, still more preferably from about 7.0 to about 7.9, and most preferably from about 7.0 to about 7.3. These relatively low pH ranges pose less risk to the gastric mucosa than existing pravastatin oral formulations having higher pH levels.

The pH of the inventive pravastatin formulations may be determined using any one of a number of methods commonly known in the art. For the purposes of reporting the pH of the formulation herein, however, the pH was measured using the following procedure. The pravastatin oral dosage forms (a number sufficient to provide 20 mg of pravastatin) were dispersed by stirring in 25 mL of room temperature water. The pH of the resulting aqueous composition was measured using a standard pH meter, such as the Beckman 360 pH/Temp/mV meter, this measurement providing the pH of the subject oral dosage form.

Despite the formulation of the inventive oral dosage forms to possess relatively low pH, the dosage forms are unexpectedly stable at these pH levels, and for unexpectedly long periods of time. In this regard, the formulations do not unduly degrade and become unusable after extended periods of time. At a minimum, the stability provided by the inventive oral formulations is at least 6 months from the date of their preparation, and is desirably stable for at least 12 months, more desirably for at least 18 months, preferably for at least 24 months, more preferably for at least 30 months, and most preferably for at least 36 months. As will be described in more detail below, stability may be measured using known accelerated methodologies for assessing formulation degradation.

The present invention contemplates pravastatin formulations suitable for oral administration. The oral formulations of the present invention may be any suitable dosage form for oral (which, for present purposes includes buccal) administration. Desirably, the oral dosage form may constitute, for example, a tablet (including but not limited to solid tablets, dissolving tablets, caplets), capsule (including hard or soft gelatin capsules, soft elastic capsules and gelcaps) or troche. The oral dosage forms further may be formulated for immediate or extended release (in the form of an extended release matrix or a plurality of particles incorporating pravastatin and a controlled release coating in each particle). Extended release dosage forms, using one or more suitable known extended release agents or coating materials are preferred.

In addition to pravastatin, the formulations of the present invention may include one or more pharmaceutically-acceptable excipients. While the amount of excipients included in the formulations may vary, the amounts should be balanced with the amount of pravastatin so as to provide a finished formulation having a pH within the ranges described herein. Generally, one may include from about 1% to about 80% excipients, with the amount desirably ranging from about 5 wt. % to about 70 wt. %, preferably from about 10 wt. %, more preferably from about 20 wt. %, and more preferably from about 30 wt. % up to about to about 40 wt. %, preferably 50 wt. % and more preferably about 60 wt. %, based on the total weight of the formulation.

The excipients found to be desirable for use in the inventive formulations are those that assist in providing the formulation with a pH that falls in the desired range. Without being bound to any particular theory, limiting or excluding those excipients that donate a proton in aqueous environments is desirable, as it is believed that excipients of this type do not inhibit degradation of the pravastatin. Examples of suitable pharmaceutically-acceptable excipients that have been found to assist in stabilizing the inventive formulations include trisodium citrate dihydrate, tripotassium citrate, sodium ascorbate, sodium citrate, corn starch, and combinations thereof. Trisodium citrate dihydrate is an especially preferred excipient for inclusion in the inventive formulations. Surprisingly, it has been found that polyvinyl pyrrolidone (PVP) and Ac-di-Sol (croscarmellose sodium) are desirably omitted from the inventive formulations, as each was found to adversely affect the stability of pravastatin formulations.

Illustrative of other desirable pharmaceutically-acceptable excipients that may be included in the present invention without adversely affecting the basic and novel characteristics thereof are binders, disintegrants and lubricants. Other optional pharmaceutically-acceptable ingredients that may be included in the inventive oral formulations include preservatives, stabilizers, anti-adherents, glidants, coloring agents, and the like.

Binders are commonly used in pharmaceutical formulations to assist in holding the various components of the formulation together, and, occasionally, used to adjust the drug-release profile of a composition, e.g., to assist in providing a formulation with a controlled-release profile. Binders, when included in preferred formulations of the invention, are desirably present in an amount of less than about 20 wt. %, more desirably less than about 15 wt. %, and preferably less than about 10 wt. %, based on the weight of the formulation. While a variety of know binders may be used in the preferred embodiments of the invention, preferred binders include cornstarch, modified cornstarch, potato starch, hydroxypropyl cellulose, and combinations thereof, with cornstarch being most preferred.

Disintegrants are typically used in oral pharmaceutical formulations to aid in the post-administration dissolution of the formulations. Disintegrants, when included in preferred formulations of the invention, are desirably present in an amount ranging from about 0.5 wt. % to about 15 wt. %, and preferably from about 1 wt. % to about 8 wt. %, based on the weight of the formulation. A variety of disintegrants may be used in the preferred embodiments of the invention. Illustrative of these are sodium starch glycolate (Explotab), crospovidone, and combinations thereof, with the use of crospovidone being preferred.

Lubricants may also be included in the preferred oral pharmaceutical formulations contemplated by the invention. Lubricants are more preferably included when the finished oral formulation is a tablet, as the lubricant can aid in the tableting process. When present, lubricants may be present in any suitable amount, desirably ranging from about 0.2 wt. % to about 5 wt. %, and more desirably from about 0.5 to about 2 wt. %, based on the weight of the formulation. Illustrative of lubricants that may be used in the present invention are magnesium stearate, calcium stearate, talc and combinations thereof, with magnesium stearate being preferred.

Fillers are commonly used in pharmaceutical formulations to increase the formulation to the desired mass/size. Preferably, and when present, the fillers desirably may be included in amounts ranging from about 5 wt. % to about 90 wt. %, more desirably from about 10 wt. % to about 70 wt. %, and more preferably from about 20 wt. % to about 60 wt. %., based on the weight of the formulation. Illustrative of fillers that may be used in the pharmaceutical formulations of the present invention are lactose, mannitol, sugar, inorganic salts such as calcium sulfate, and combinations thereof, the filler preferably being lactose.

When the excipients are selected and used in amounts that result in the finished oral pravastatin formulation having a pH within the ranges recited herein, there is no need to include a basifying agent or a pH-adjusting buffering agent. Such agents have been used in existing compositions to increase the pH of the formulations to a relatively high pH. Desirably, then, the inventive formulations include only a minimal amount of a buffering agent (less than about 5 wt. %, preferably less than about 3 wt. %), and is preferably substantially free, or more preferably completely free, of buffering and basifying agents. Illustrative of buffering agents used in known formulations are sodium citrate, magnesium aluminum silicate; illustrative basifying agents include sodium phosphate.

The inventive oral pharmaceutical formulations of the present invention may be prepared using the aforementioned ingredients in any of the recited ranges or amounts. In this regard, one preferred oral pravastatin pharmaceutical formulation contemplated by the present invention comprises about 3 wt. % to about 50 wt. % of pravastatin sodium, about 10 wt. % to about 80 wt. % lactose, less than about 10 wt. % cornstarch, about 2 wt. % to about 8 wt. % crospovidone, about 1.5 wt. % to about 5 wt. % trisodium citrate dihydrate, and about 0.5 wt. % to about 2 wt. % magnesium stearate. In this embodiment, the pH ranges from about 7 to about 7.5.

In a related embodiment, the present invention provides a stable oral pravastatin composition comprising a physical mixture of pravastatin and at least one pharmaceutically-acceptable excipient, wherein the composition for at least 6 months (and desirably for at least 12 months, more desirably for at least 18 months, preferably for at least 24 months, more preferably for at least 30 months, and most preferably for at least 36 months) after its preparation, after being placed in a sealed container, comprises less than about 2% lactone after residing for 3 months in a stability chamber set at 40° C. and 75% relative humidity.

The stability of the inventive composition is measured by the percentage of degradant formed over time, relative to the dosage of pravastatin in the formulation. The presence of one such degradant, lactone, may be used to quantify the stability of a formulation. Thus, one means of determining the relative stability of a pravastatin formulation is by measuring the amount of lactone (in wt. % relative to the total formulation) present in the formulation at a specific time. An increase in the lactone content of a pravastatin formulation over time (e.g., as compared to an earlier determination of lactone content) evidences a decrease in stability of the pravastatin formulation.

For purposes of the present invention, the lactone content of an oral pravastatin formulation may be measured after the formulation is placed in a sealed container with a desiccant and cotton and subjected to an accelerated degradation study. In this study, the container (in which the formulation resides) is placed in a chamber set at a relatively high temperature (40° C.) and humidity (75% relative humidity) for three months, after which the formulation is analyzed for lactone content.

When the inventive formulation is an oral dosage form comprising about 10 mg of pravastatin (or representative proportions thereof, e.g., 20 mg, 40 mg, etc.), the pH of the formulation is about 7 to less than 9, and the formulation is placed in a sealed container on the preparation date: (a) after about one month in the 40° C./75% RH stability chamber, the formulation comprises less than about 0.61 wt. % (e.g., 0.6 wt. %) lactone, more preferably less than about 0.5 wt. %, even more preferably less than about 0.2 wt. %, still more preferably less than about 0.1 wt. %, and most preferably less than about 0.05 wt. % lactone; (b) after about two months in the 40° C./75% RH stability chamber, less than about 1.21 wt. % (e.g., 1.2 wt. %), more preferably less than about 1 wt. %, even more preferably less than about 0.5 wt. %, still more preferably less than about 0.3 wt. % (e.g., 0.28 wt. %), and most preferably less than about 0.15 wt. % (e.g., 0.14 wt. %) of the formulation comprises lactone; and (c) after about three months in the stability chamber, which is designed to simulate two-years of shelf life from the date of preparation, less than about 2.05 wt. % (e.g., 2 wt. %), more preferably less than about 1.5 wt. %, even more preferably less than about 1 wt. %, still more preferably less than about 0.5 wt. % (e.g., 0.41 wt. %), and most preferably less than about 0.25 wt. % of the formulation comprises lactone.

The inventive formulations also experience a reduction in lactone formation relative to the lactone formation arising in known pravastatin formulations when placed, in a sealed container, in a chamber set at 40° C./75% RH even when the stability evaluation is not commenced on the formulation preparation date. The same methodology described above applies. Indeed, the preferred pravastatin formulations of the present invention are stable, e.g., they exhibit the claimed pH levels, lactone content and/or Impurity A content, if placed in a sealed container with a desiccant and cotton, with the container placed in a stability chamber set at 40° C. and 75% RH, at various intervals after its preparation. For example, the formulation is desirably stable at 3 months, 6 months, 9 months, 12 months, 18 months, 24 months, 30 months, and at 36 months from it date of preparation.

Another aspect of the present invention relates to the discovery of a new impurity in pravastatin formulations, referred to as Impurity A, and a means of identifying this impurity. It was further found that Impurity A may be used in assessing the stability of a pravastatin formulation. For example, the stability of a pravastatin formulation may be determined by measuring the amount of Impurity A, i.e., the wt. % of Impurity A based on the total weight of the formulation, in a particular pravastatin formulation.

Thus, in a further embodiment, the invention provides an oral pravastatin composition comprising pravastatin, wherein the composition for at least 6 months (and desirably for at least 12 months, more desirably for at least 18 months, preferably for at least 24 months, more preferably for at least 30 months, and most preferably for at least 36 months) after its preparation, after being placed in an unsealed container, comprises less than about 0.34 wt. % of a heretofore unknown impurity (referred to herein as Impurity A) after residing for 1 week in a stability chamber set at 55° C. and 75% relative humidity.

Figure 2:
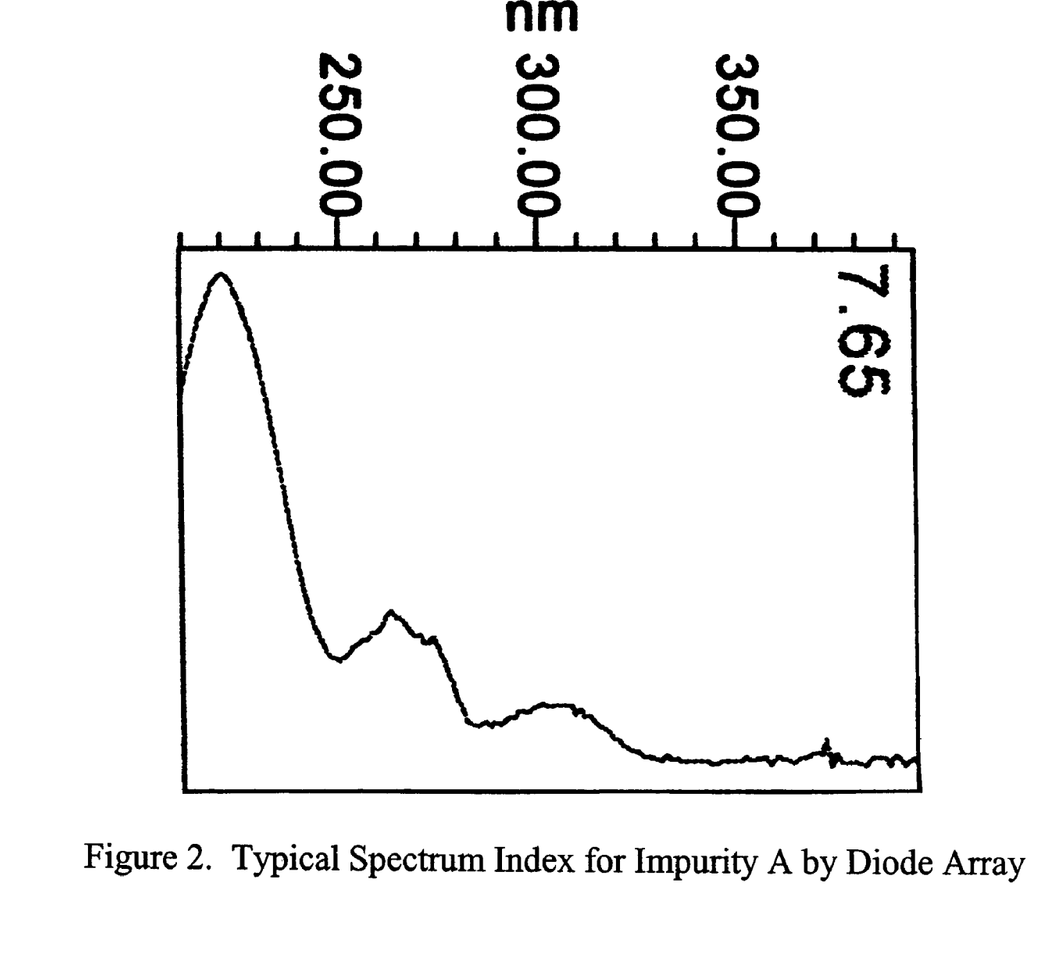
FIG. 2 is a representative spectrum index for Impurity A by diode array analysis.
Figure 3:
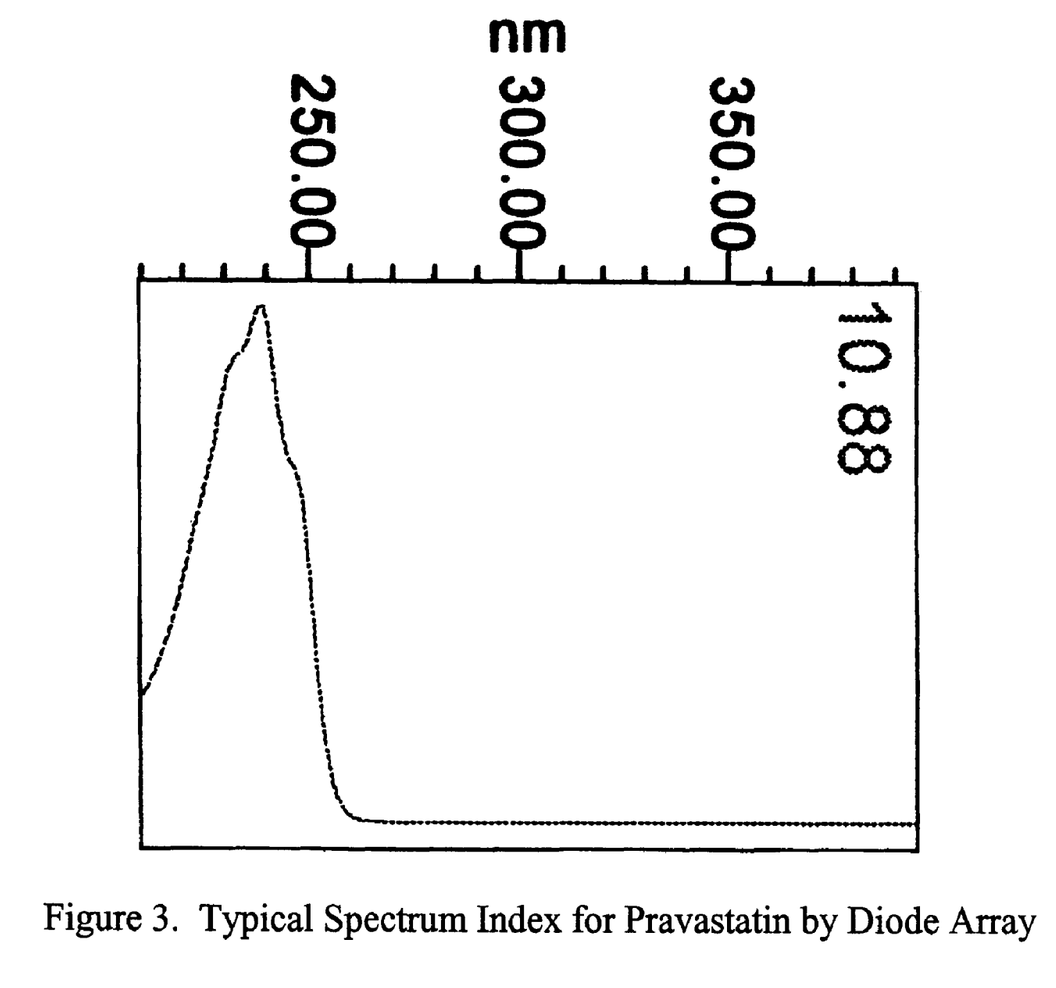
FIG. 3 is a representative spectrum index for pravastatin by diode array analysis.
Figure 4:
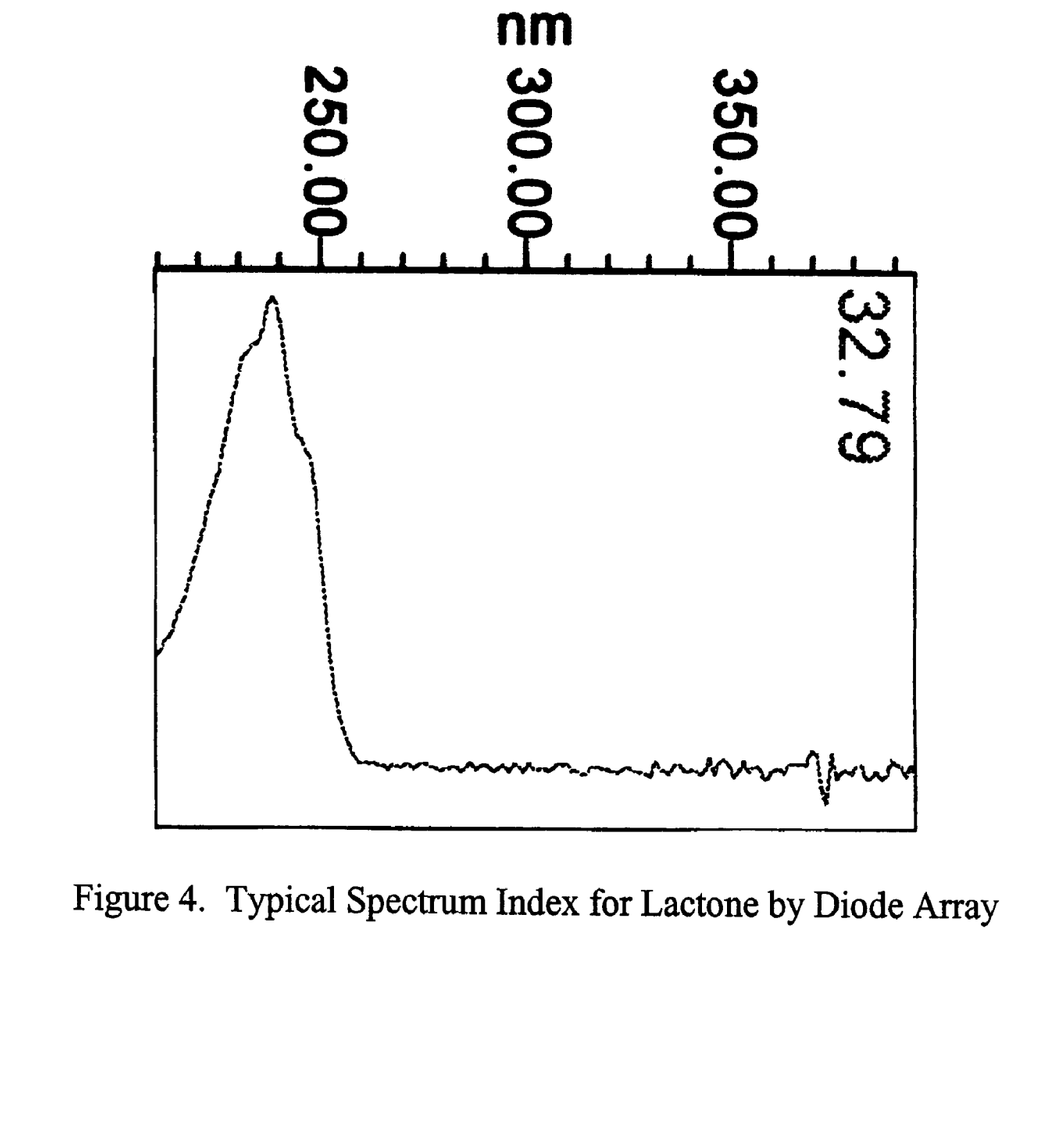
FIG. 4 is a representative spectrum index for lactone by diode array analysis.

Data useful in identifying Impurity A may be found in FIGS. 2-4, as described in more detail below.

For purposes of the present invention, Impurity A may be measured using either open dish or closed dish accelerated degradation studies.

Closed dish acceleration studies involve placing the pravastatin formulation in a sealed container with a desiccant and cotton, with the sealed container being placed in a stability chamber set at 40° C. and 75% RH for three months. After about three-months in the stability chamber, pravastatin formulations (i.e., on a 10 mg pravastatin basis) comprises less than about 0.2 wt. %, preferably less than about 0.15 wt. %, even more preferably less than about 0.125 wt. %, still more preferably less than about 0.11 wt. %, and most preferably less than about 0.1 wt. %, of Impurity A.

Open dish accelerated degradation studies may be conducted in a stability chamber set at a temperature of 55° C. and 75% RH. Open dish studies reflect storage and handling conditions often encountered during the shelf life of the tablets. In the open dish study used in connection with the present invention, pravastatin formulations (commonly tablets) are placed in open petri dishes, which are in turn placed into the stability chamber (set at 55° C./75% RH). Degradation (Impurity A levels) are measured at one week and/or one month intervals.

Preferred pravastatin formulations of the present invention, after one-week in the stability chamber, comprise less than about 0.36 wt. %, more preferably less than about 0.3 wt. %, even more preferably less than about 0.2 wt. %, still more preferably less than about 0.1 wt. %, and most preferably less than about 0.08 wt. % of Impurity A.

Pravastatin, lactone and Impurity A may be identified by any suitable method known in the art. For purposes of the present invention, as further discussed herein, pravastatin, lactone and Impurity A were separated from a pravastatin composition by HPLC, wherein the mobile phase consisted of a gradient with component A (80% buffer with pH of 7.0 and 20% acetonitrile) and component B (100% acetonitrile), the 150 mm×4.6 mm column being packed with L1 packing (Waters Xterna RP 18 5µ). The flow rate was 1 ml/min, with an injection volume of 20 µl. The column was at ambient temperature and the sample temperature was 8° C. The gradient was programmed as follows:

| Time (min) | % A | % B |
| --- | --- | --- |
| 0 | 100 | 0 |
| 15 | 100 | 0 |
| 25 | 87.5 | 12.5 |
| 35 | 87.5 | 12.5 |
| 40 | 62.5 | 37.5 |
| 54 | 62.5 | 37.5 |
| 55 | 100 | 0 |

The column also contained a UV detector adjusted to about 238 nm. A chromatogram may then be generated from the HPLC, as well as spectrum indices by diode array from the UV detector.

Figure 1:
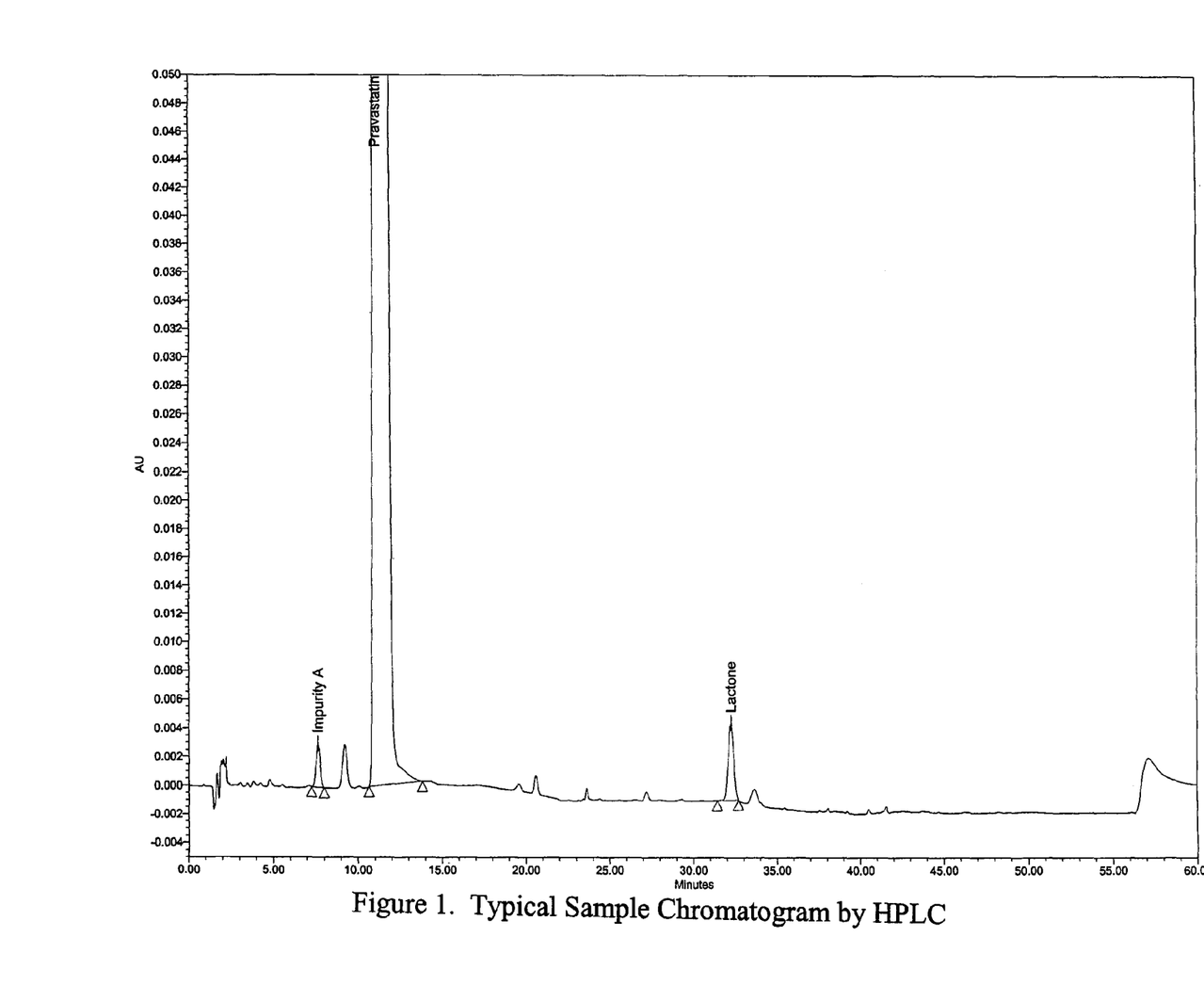
FIG. 1 is a chromatogram by HPLC of Provacol® containing 10 mg of pravastatin after a closed dish accelerated degradation study conducted in a stability chamber set at a temperature of 40° C. and 75% relative humidity.

FIG. 1 is a chromatogram by HPLC of Provacol® containing 10 mg of pravastatin after a closed dish accelerated degradation study was conducted in a stability chamber set at a temperature of 40° C. and 75% relative humidity. As shown in FIG. 1, the retention time of Impurity A is from about 7.3 minutes to about 8.3 minutes; pravastatin from about 10.1 minutes to about 12.1 minutes; and lactone from about 30.5 minutes to about 34.2 minutes. Because the retention times may vary depending on the conditions of the HPLC, a more meaningful identification of these components by HPLC is relative retention time, i.e., the retention time relative to pravastatin. From FIG. 1, the relative retention time of Impurity A is from about 0.68 to about 0.72; pravastatin is 1; and lactone from about 2.7 to about 3.2. As shown in FIG. 2, the spectrum index for Impurity A by diode array shows three maximum peaks at 221 nm±1 nm, 265 nm±1 nm, and 303 nm±1 nm. As shown in FIG. 3, the spectrum index for pravastatin by diode array is 239 nm±1 nm. As shown in FIG. 4, the spectrum index for lactone by diode array is 239 nm±1 nm.

A further aspect of the present invention provides a process for preparing the inventive oral pravastatin formulations described herein, which process includes physically mixing pravastatin with one or more excipients.

In an illustrative physical mixing process suitable for the preparation of oral tablet (or capsule) formulations by direct compression, the excipients are preferably milled until 100% of each excipient passes through a #80 mesh screen. A portion of the milled excipients may then be mixed with pravastatin. The resulting mixture may then, if desired, be milled through a #40 mesh screen, with the remaining portion of the excipients passed through the same screen. The resulting milled components may then be physically mixed together, followed by addition of a lubricant, and further mixed until a final homogeneous mixture results. This final mixture can then be compressed into tablets, each tablet containing, e.g., 10 mg, 20 mg, 40 mg or 80 mg of pravastatin. Alternately, the mixture can be extruded and cut into beads to form capsules.

Illustrative of a wet granulation process useful in the preparation of tablets or capsules, a portion of the total amount of excipients may be dissolved in water or an ethanol-water mixture. The resulting mixture can then be used to granulate, for example, a mixture of a portion of the remaining excipients. The granulated mixture is then preferably passed through a #3 to #12 mesh screen and dried in a fluid-bed. The resulting dried granulates are then preferably milled through a #20 to #40 mesh screen. The remainder of the excipients may then be added and mixed until a final homogeneous mixture results. The final mixture can then be compressed into tablets, each tablet containing e.g., 10 mg, 20 mg, 40 mg, and 80 mg of pravastatin. Alternately, the mixture can be extruded and cut into beads to form capsules.

In a further aspect, the invention contemplates therapeutic methods of using the aforementioned stable dosage forms of pravastatin. More specifically, the inventive methods contemplate administering to an animal, desirably a human in need of the following therapy, an effective amount of the inventive stable oral pravastatin formulations described herein. Therapies for which the inventive formulations may be used include: (a) the primary prevention of coronary events (in hypercholesterolemic patients without clinically evident coronary heart disease) to reduce the risk of: myocardial infarction; undergoing myocardial revascularization procedures; and cardiovascular mortality with no increase in death from non-cardiovascular causes; (b) the secondary prevention of cardiovascular events (in patients with clinically evident coronary heart disease) to reduce the risk of total mortality by reducing coronary death; to reduce the risk of myocardial infarction; to reduce the risk of undergoing myocardial revascularization procedures; to reduce the risk of stroke and stroke/transient ischemic attack (TIA); and to slow the progression of coronary atherosclerosis; and (c) hyperlipidemia: as an adjunct to diet to reduce elevated total-C, LDL-C, Apo B and TG levels and to increase HDL-C in patients with primary hypercholesterolemia and mixed dyslipidemia; as adjunctive therapy to diet for the treatment of patients with elevated serum triglyceride levels; and in the treatment of patients with primary dysbetalipoproteinemia who do not respond adequately to diet; and as an adjuct to diet and life-style modification for treatment of HeFH in children and adolescent patients ages 8 years and older if after an adequate trial of diet the following findings are present: 1) LDL-C remains at least equal to 190 mg/dL or LDL-C remains at least equal to 160 mg/dL and there is a positive family history of premature cardiovascular disease or two or more other CVD risk factors are present in the patient.

The following examples further illustrate the invention but, of course, should not be construed as in any way limiting its scope. All temperatures are expressed in degrees Centigrade and all mesh sizes are U.S. Standard ASTME.

EXAMPLES

In the examples, pH of the commercial products was measured by dispersing tablet(s) of 80 mg equivalent in 100 ml of water. For the tablets of the inventive compositions, the pH was measured by dispersing tablet(s) of 20 mg equivalent in 25 mL of water. The pH was measured using a standard pH meter, such as the Beckman 360 pH/Temp/mV Meter.

Example 1

In this example, a preferred embodiment of the pravastatin formulations of the present invention prepared by physically mixing the components until a homogenous mixture is obtained followed by direct compression to provide a tablet.

| INGREDIENT | WT. % |
| --- | --- |
| Pravastatin | 10 |
| Lactose (fast-flo) | 81 |
| Crospovidone | 5 |
| Trisodium citrate dihydrate | 3 |
| Magnesium stearate | 1 |

Example 2

This example sets forth another preferred pravastatin formulation of the present invention prepared by physically mixing the components until a homogenous mixture is obtained followed by direct compression to provide a tablet.

| INGREDIENT | WT. % |
| --- | --- |
| Pravastatin | 10 |
| Lactose (fast-flo) | 83 |
| Crospovidone | 4 |
| Trisodium citrate dihydrate | 1.5 |
| Magnesium stearate | 1.5 |

Example 3

This is yet another example of a preferred pravastatin formulation of the present invention.

| INGREDIENT | WT. % |
|---|---|
| Pravastatin | 10 |
| Lactose | 81 |
| Crospovidone | 5 |
| Sodium citrate | 3 |
| Magnesium stearate | 1 |

The sodium citrate was milled to a fine powder, and was then mixed with pravastatin, crospovidone and a portion of lactose. The mixture was then milled through #20 to #40 mesh screen, and the remaining portion of lactose was passed through the same screen. The resulting mixture was thoroughly mixed. Magnesium stearate was then added and mixed for 1 to 3 minutes. The resulting final mixture was compressed into tablets.

Example 4

A further example of a preferred pravastatin formulation of the present invention.

| INGREDIENT | WT. % |
|---|---|
| Pravastatin | 10 |
| Lactose | 83 |
| Crospovidone | 4 |
| Sodium citrate | 1.5 |
| Magnesium stearate | 1.5 |

The sodium citrate was milled to a fine powder, which was then mixed with pravastatin, crospovidone and a portion of lactose. The mixture was then milled through #20 to #40 mesh screen, and the remaining portion of lactose was passed through the same screen. The resulting mixture was mixed. Magnesium stearate was then added and mixed for 1 to 3 minutes. The resulting mixture was compressed into tablets.

Example 5

This example demonstrates the stability of preferred pravastatin formulations of the present invention having a pH of less than about 7.5 (as described in Examples 3 and 4) relative to Pravachol® tablets which have a pH of 10.0. Accelerated degradation studies were conducted in a stability chamber set at a temperature of 40° C. and 75% RH. Sealed bottles containing the subject pravastatin pharmaceutical formulations, a desiccant and cotton were placed in the stability chamber, with the extent of degradation measured in one-month intervals. Three-months in the stability chamber is intended to simulate a two-year shelf life from the date of manufacture. The stability of the pravastatin formulations was measured by determining the percentage of lactone present therein. An increasing percentage of lactone over time correlates to an increase in pravastatin formulation degradation, and indicates a decrease in formulation stability.

| | | % Lactone | | |
|---|---|---|---|---|
| | pH | Initial | 1-month | 3-months |
| Pravachol ® 10 mg (1 year prior to expiration date) | 10 | 0.45 | 0.61 | 2.05 |
| Pravachol ® 20 mg (1.5 years prior to expiration date) | 10 | 0.35 | 0.46 | 1.5 |
| Pravachol ® 80 mg (2.5 years prior to expiration date) | 10 | 0.03 | 0.1 | 0.27 |
| Example 3 | 7.3 | 0.05 | 0.14 | 0.25 |
| Example 4 | 7.0 | 0.04 | 0.10 | 0.41 |

Example 6

This example demonstrates a preferred dry blend granulation process that may be used to prepare preferred stable oral pravastatin pharmaceutical formulations of the present invention. 30 grams of trisodium citrate was milled until 100% of this excipient passed through a #80 mesh screen. The milled trisodium citrate was then mixed with 100 grams of pravastatin, 50 grams of crospovidone, and 404.25 grams of lactose. The total mixture was then milled through mesh screens #20 to #40, at which time 404.25 grams of lactose were passed through the same screen. The resulting mixture was mixed for 15 minutes. 10 grams of magnesium stearate was added to the mixture and mixed for an additional 1 to 3 minutes. The resulting final mixture was compressed into about 10,000 100 mg pravastatin tablets.

Example 7

This example demonstrates a preferred wet granulation process useful in preparing a preferred stable oral pravastatin pharmaceutical formulation of the present invention. 30 grams of trisodium citrate was dissolved in 200 grams of water. The resulting mixture was then used to granulate a mixture of 485.1 grams of lactose and 30 grams of crospovidone. The granulated mixture was then passed through a #3 to #12 mesh screen and dried in a fluid-bed drier for 15 minutes. The dried granulates were then milled through a #20 to #40 mesh screen. Next, 20 grams of crospovidone, 323.1 grams of lactose and 10 grams of magnesium stearate were added thereto and mixed for about 15 minutes until a final homogeneous mixture is obtained. The resulting final mixture was compressed into about 10,000 100 mg pravastatin tablets.

Example 8

This example provides another illustration of a preferred stable oral pharmaceutical formulation of the present invention.

| INGREDIENT | WT. % |
|---|---|
| Pravastatin sodium | 10 |
| Mannitol | 66 |
| Microcrystalline Cellulose | 13 |
| Corn Starch | 6 |
| Crospovidone | 4 |
| Magnesium stearate | 1 |

Pravastatin sodium, microcrystalline cellulose, corn starch, and part of mannitol were granulated with water. The granules were then dried and milled. The remainder of the mannitol and crospovidone were then mixed with the granules. The magnesium stearate was then mixed therein, and the resulting composition was compressed into tablets.

Example 9

This example provides yet another illustration of a preferred stable oral pharmaceutical formulation of the present invention.

| INGREDIENT | WT. % |
|---|---|
| Pravastatin sodium | 10 |
| Mannitol | 66 |
| Microcrystalline Cellulose | 13 |
| Corn Starch | 6 |
| Sodium Starch glycolate | 4 |
| Magnesium stearate | 1 |

Pravastatin sodium, microcrystalline cellulose, corn starch, and part of mannitol were granulated with water. The granules were dried and milled. The remainder of the mannitol and sodium starch glycolate were then mixed with the granules. The magnesium stearate was then mixed in, and the resulting composition was compressed into tablets.

Example 10

This example demonstrates the stability of a preferred oral pravastatin formulation of the present invention having a pH of less than about 7.5 relative to Pravachol® which has a pH of 10.0. Accelerated degradation studies were conducted in a stability chamber set at a temperature of 55° C. and 75% RH. The open stability study was performed by placing the tablets onto an open petri dish, and then placing the petri dish into the stability chamber. On exposure to moisture in the presence of high pH (greater than 9), lactone formation was prohibited. However, there was an appreciable increase in the amount of Impurity A in the Pravachol® tablets, but not in the tablets of the present invention (Examples 8 and 9).

|  | pH | % Lactone | | % Impurity A | |
|---|---|---|---|---|---|
|  |  | Initial | 1-week | Initial | 1-week |
| Pravachol ® 10 mg (1 year prior to expiration date) | 10 | 0.45 | 0.04 | 0.02 | 0.48 |
| Pravachol ® 20 mg (1.5 years prior to expiration date) | 10 | 0.35 | 0.03 | 0 | 0.34 |
| Pravachol ® 40 mg (2 years prior to expiration date) | 10 | 0.25 | 0.03 | 0 | 0.36 |
| Example 8 | 7.0 | 0.06 | 0.23 | 0.04 | 0.08 |
| Example 9 | 7.1 | 0.06 | 0.17 | 0.04 | 0.08 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for prophylactic treatment of coronary events, prophylactic treatment of cardiovascular events or therapeutic treatment of hyperlipidemia in a human in need thereof, which method comprises administering to the human an effective amount of a stable oral pravastatin formulation consisting of a physical mixture of 10 wt. % pravastatin sodium, 66 wt. % mannitol, 13 wt. % microcrystalline cellulose, 6 wt. % corn starch, 4 wt. % crospovidone or sodium starch glycolate, and 1 wt. % magnesium stearate, wherein, when an amount of the formulation sufficient to provide 20 mg of pravastatin is dispersed by stirring in 25 mL of room temperature water, the formulation has a pH in the range of about 7 to about 7.5, whereupon said human is treated.

2. The method of claim 1, wherein the formulation, upon placement of the formulation on the day of preparation onto an open Petri dish and placed into a stability chamber set at 55° C. and 75% relative humidity, contains 0.23 wt. % or less of lactone and 0.08 wt. % or less of Impurity A after the formulation has been in the open dish in the stability chamber for at least 1 week.

3. The method of claim 1, wherein the human is in need of prophylactic treatment of a coronary event.

4. The method of claim 1, wherein the human is in need of prophylactic treatment of a cardiovascular event.

5. The method of claim 1, wherein the human is in need of therapeutic treatment of hyperlipidemia.

6. The method of claim 2, wherein the human is in need of prophylactic treatment of a coronary event.

7. The method of claim 2, wherein the human is in need of prophylactic treatment of a cardiovascular event.

8. The method of claim 2, wherein the human is in need of therapeutic treatment of hyperlipidemia.

* * * * *